United States Patent [19]

Sanford et al.

[11] Patent Number: 5,186,807
[45] Date of Patent: Feb. 16, 1993

[54] ELECTROPHORESIS GEL SLAB CASSETTES HAVING PULL CORDS AND METHODS

[75] Inventors: David P. Sanford, Portsmouth; Bruce R. Turner, Fremont; Richard J. Heim, Exeter, all of N.H.

[73] Assignee: Erie Scientific Company, Portsmouth, N.H.

[21] Appl. No.: 744,484

[22] Filed: Aug. 13, 1991

[51] Int. Cl.$^5$ ............... G01N 27/26; B01D 57/02
[52] U.S. Cl. ........................ 204/299 R; 204/182.8
[58] Field of Search ............ 204/299 R, 182.8; 220/270, 269, 271, 272

[56] References Cited

U.S. PATENT DOCUMENTS

| | | | |
|---|---|---|---|
| 4,211,336 | 7/1980 | Helms | 220/270 |
| 4,434,908 | 3/1984 | French | 220/276 |
| 4,548,333 | 10/1985 | Kobayashi et al. | 220/276 |
| 4,929,329 | 5/1990 | Danby et al. | 204/299 R |

Primary Examiner—John Niebling
Assistant Examiner—John S. Starsiak, Jr.
Attorney, Agent, or Firm—Wood, Herron & Evans

[57] ABSTRACT

Novel vertical electrophoresis cassettes having pull cords for opening the cassettes following electrophoresis runs are disclosed. Uniquely, the electrophoresis cassettes have pull cord assemblies positioned along the opposing vertical side edges of the front and back plates and between the front and back plates. More particularly, the pull cord assembly comprises a pull tab integrally connected to a tear strip. The front and back plates of the electrophoresis cassette are held together by either a soft-curing adhesive or adhesive tape positioned along the opposing vertical side edges of the cassette. The tear strip of the pull tab assembly is positioned between the adhesive or adhesive tape and spacers. To open the cassette, the pull tab is grabbed and the tear strip rips through the adhesive or adhesive tape to open the cassette along one vertical side thereof. Once the pull cord assembly has torn through the adhesive or adhesive tape, the front plate can be opened about a hinge formed by the adhesive tape or adhesive along the opposite vertical side edge of the cassette. Of course, the pull cord assembly along the opposite vertical side edge of the cassette may also be pulled and torn through the adhesive or adhesive tape so that the front and back plates may simply be pulled apart from one another.

16 Claims, 3 Drawing Sheets

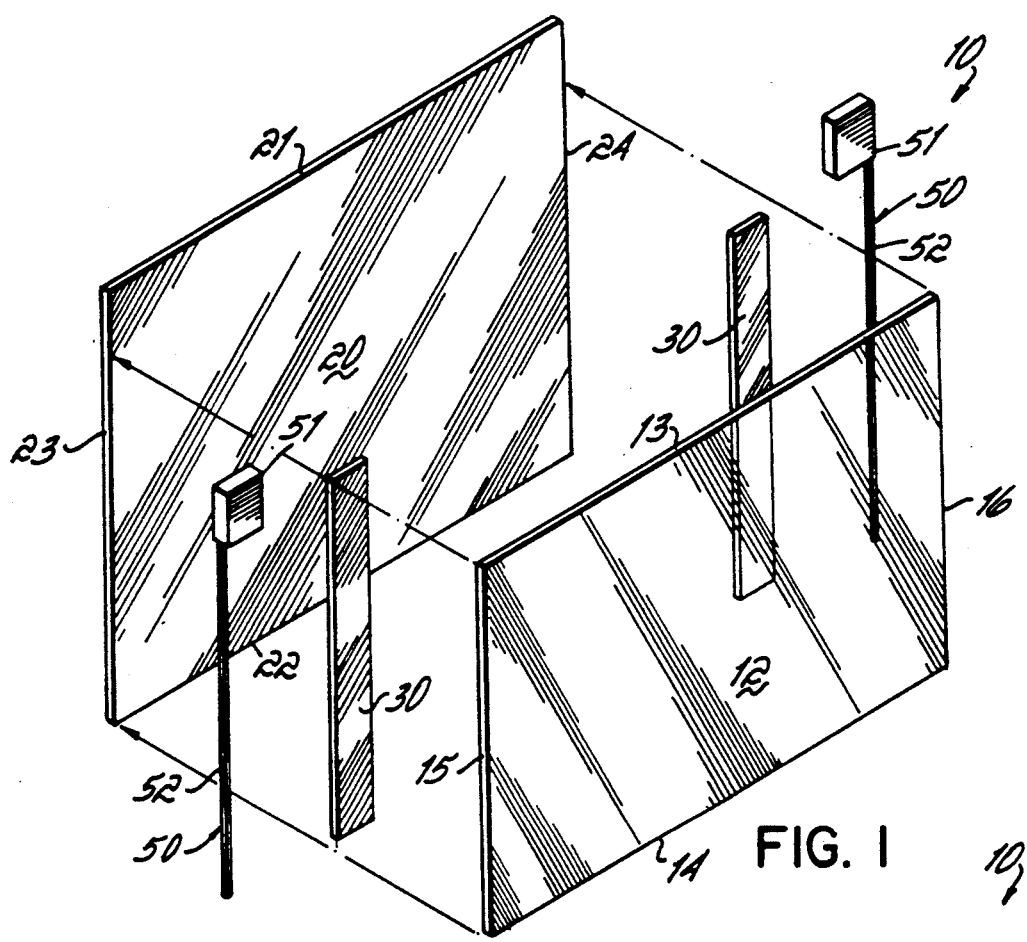
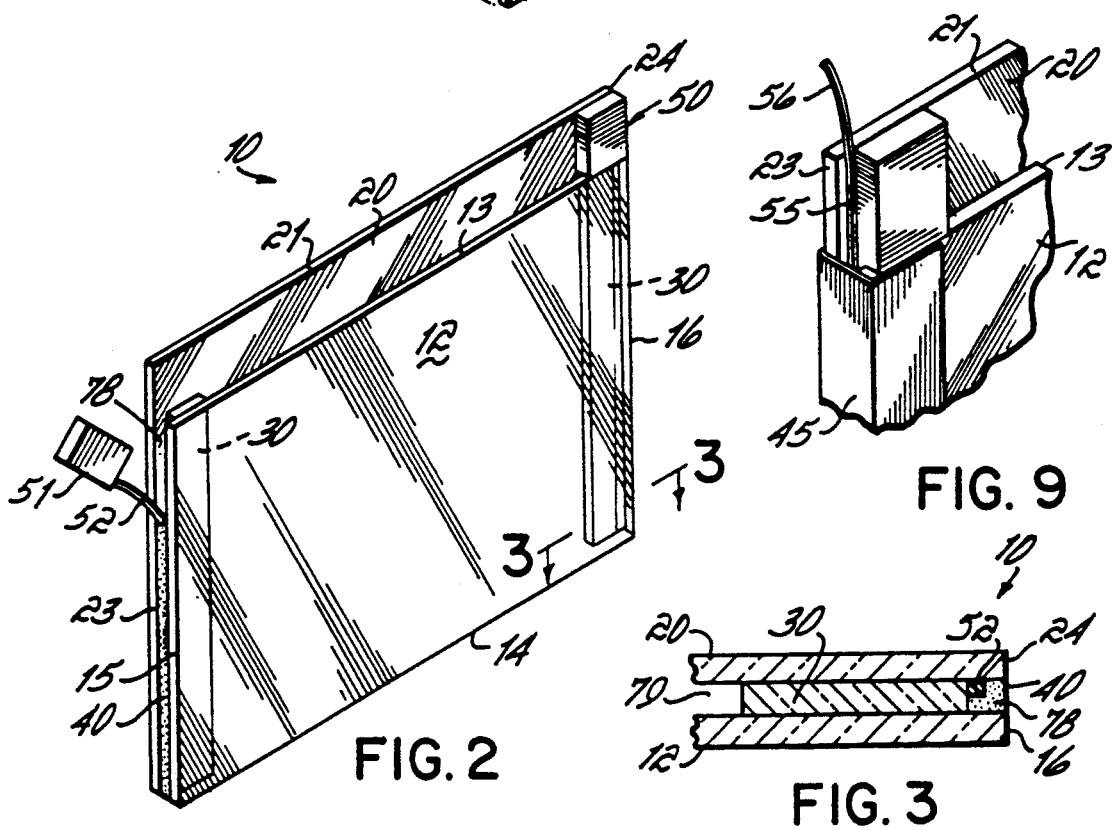

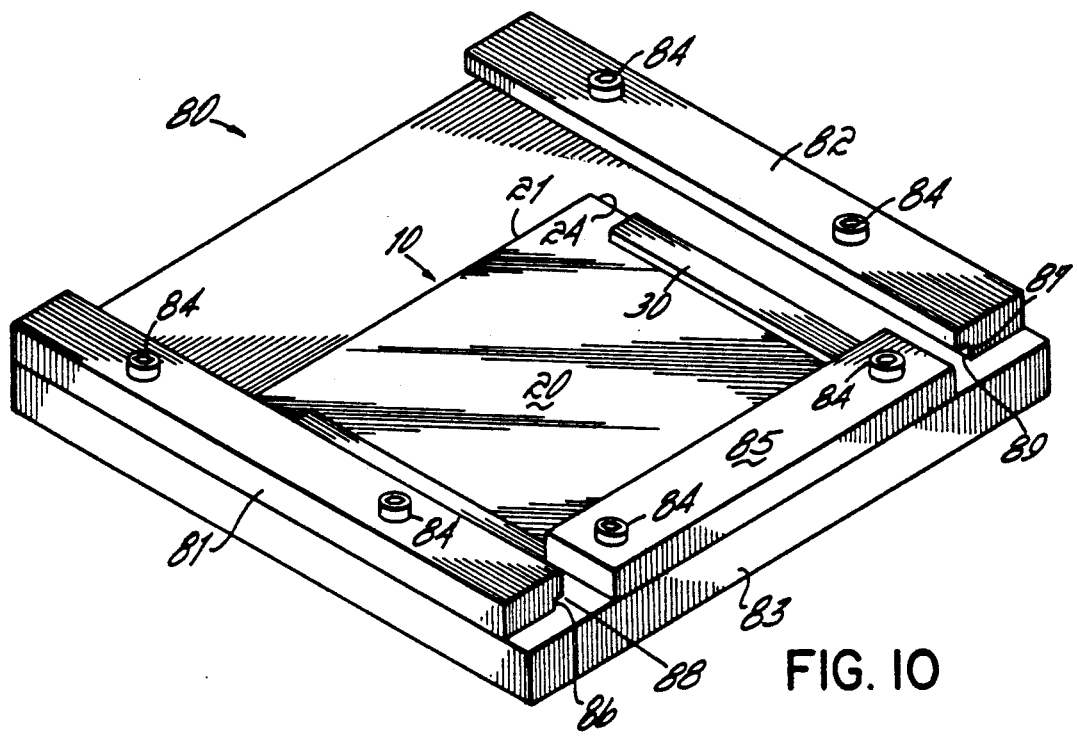
FIG. 10
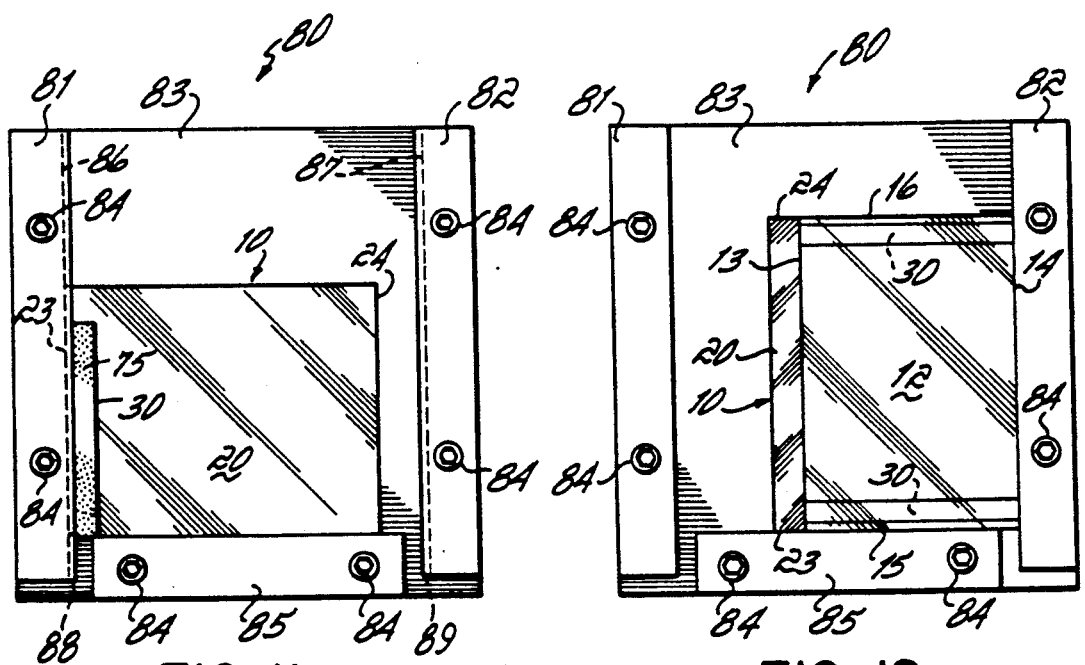
FIG. 11
FIG. 12

ELECTROPHORESIS GEL SLAB CASSETTES HAVING PULL CORDS AND METHODS

FIELD OF THE INVENTION

The present invention relates to novel electrophoresis gel slab cassettes, each being formed with two non-conductive plates spaced apart from one another via spacers and including at least one pull cord positioned between the plates along the left and/or right side vertical edges of the plates for facilitating the separation of the two plates following electrophoresis, so that the gel slab cast between the two plates can be removed therefrom and the biological molecules electrophoresed therein can be analyzed. The instant invention further relates to methods for using and making the novel electrophoresis cassettes.

BACKGROUND

Electrophoresis involves the separation of charged molecules in an electric field. It is based upon the principle that an electric field will cause charged molecules to migrate into separate factions. Usually, separation of the charged molecules is based on the strength of the electrical field and the net charge, size and shape of the molecules. The rate of separation can also be based on other parameters, such as the isoelectric points, ionic strength, viscosity, and temperature of the medium in which the charged molecules are moving. Since proteins and other biological molecules, such as DNA, RNA, enzymes, carbohydrates and the like are charged, electrophoresis techniques are ideal to separate them for either analytical or preparative purposes.

Electrophoresis is generally performed in gels cast in tubes, slabs or on flat beds. A tube gel unit is formed in a glass tube which is typically 12 cm. in length and between about 3 and 5 mm. in internal diameter. In a gel slab, the gel is formed between two non-conducting plates spaced apart by two spacer strips at the edges and clamped together to make a water-tight seal. The gel tube units and gel slab cassettes are mounted vertically. The flat bed gel units, on the other hand, are mounted horizontally since the gels are poured on horizontal surfaces and they do not include top plates.

Gel electrophoresis devices may be broadly categorized as vertical gel electrophoresis devices or as horizontal gel electrophoresis devices. Typically, the vertical gel electrophoresis devices include a bottom tank and a top tank removably situated inside the bottom tank so as to provide two spaces for electrolytes, i.e., a first or lower space between the respective walls of the bottom and top tanks and a second or upper space inside the top tank. Both tanks include a vertically extending electrophoresis gel slab cassette, which contains a gel slab for separation of a mixture of charged biological molecules, and separate electrodes. In the electrophoresis devices, the only intended path for electricity is from the electrode in the top space to an electrode in the bottom space, via electrolytes in the top space, the gel and electrolytes in the bottom space, in that order. Buffer solutions are generally selected to function as the electrolytes in the tanks. To prevent the gel electrophoresis devices from shorting out and to force the electric current through the gel slab, it is imperative that the buffer solution in the top space remain separated at all times from the buffer solution in the bottom space. In other words, the electrical connection between the two electrodes is only through the gel slab.

As indicated, electrophoresis cassettes typically include a slab of gel cast in a sandwich-type arrangement between two die-electric or non-conducting flat plates, such as glass, to form a sheet of gel between the glass surfaces. Clear glass plates are generally selected to permit monitoring of the gel-forming solution as it is injected into the space between the plates, as well as monitoring of the finished gel as electrophoresis is taking place. While the gels used in the different types of electrophoresis cassettes may vary in shape, a common gel configuration is that of a thin, flat slab being generally of uniform thickness. The glass plates of electrophoresis cassettes are typically separated by thin, flat, rectangular-shaped spacer strips positioned between the glass plates and along their opposing vertical side edges. The electrophoresis cassettes are generally held together by clamps at each vertical edge to form the water-tight seals. To accomplish this, the clamps typically extend along the entire length of the opposing vertical side edges of the glass plates of the electrophoresis cassettes.

In performing an electrophoresis separation of a mixture of charged biological molecules, the surfaces at each end of the gel slab are connected to separate electrodes via the buffer solutions. A potential is applied across the gel slab by connecting each buffer solution to opposite polarities of a voltage source. The mixture of charged biological molecules to be sorted is placed at the negative electrode end of the gel slab, usually in preformed wells. The electrical field applied across the gel slab reacts with the negative charges on the biological molecules to provide a force propelling the charged biological molecules through the gel slab towards the positive electrode. Smaller charged biological molecules have less resistance to travelling through the gel slab than larger charged biological molecules, resulting in a separation and sorting of the biological molecules by size as they migrate through the gel slab.

Following electrophoresis runs, the gels can be analyzed by staining or autoradiography followed by densitometry, or by blotting to a membrane for nucleic acid hybridization, autoradiography or immunodetection. The autogradography method relied upon to view the electrophoretic separation of charged biological molecules in a gel slab involves, for instance, the use of radio-labeled molecules. Typically, the gel slab used for electrophoresis is removed from its cassette following the electrophoresis run and placed along side a photographic medium which is exposed by the radioactive emissions of the radio-labeled biological molecules. Developing the emissions in the photographic medium produces a series of stripes representative of the position of each set of radio-labeled biological molecules. In other words, the migration patterns of multiple rows obtained after the migration, i.e., a group of zones formed by electrophoresis on the gel slab, is recorded as an autoradiogram. When the mixture of charged biological molecules consists of DNA or RNA molecules, the base arrangement of the DNA or RNA molecules are determined by comparing positions of the separated zones in the respective rows with one another.

In the more common method relied upon to view the electrophoretic separation of charged biological molecules in a gel slab, it involves the use of a stain to stain the migrated molecules. This method generally involves removing the gel slab used for electrophoresis from its cassette following the electrophoresis run and exposing it to, for example, Coomassie Blue to stain the separated fractions to also produce a series of visible stripes representative of the position of each set of stained biological molecules. The molecular weights of the charged biological molecules, such as proteins, can be determined by comparing positions of the stained stripes in the respective rows with one another and against a row of visible stripes formed with markers having known molecular weights. In addition to Coomassie Blue, the separated molecules may be stained by photographic amplification systems using silver or other first row transition metals.

The comparison in either of the above recited methods is carried out based o the electrophoresis principle that charged biological molecules having equal molecular weights, charges and shapes migrate by equal distances if the electrophoresis is started from the same line and under the same conditions, such as ionic strength, viscosity and temperature.

While vertical electrophoresis gel slab cassettes have been successfully used up to now to carry out electrophoresis, they are not without drawback. During the initial assembly, the vertical electrophoresis gel slab cassettes available heretofore are generally assembled with tape running along the entire opposing vertical side edges of the two glass plates to hold the cassettes together. This obviously is a labor intensive and inconvenient method to assemble the cassettes. In addition, certain tapes available are not suitable to use due to the incompatibility between the adhesives on the tapes and the buffer solutions selected to carry out the electrophoresis. More importantly, when it is time to remove the gel slabs from the cassettes following the electrophoresis runs, the tape must be cut with, for example, a razor blade or sharp knife, since it will often tear, if peeled uncut, making it more difficult to remove. Another disadvantage associated with this method of opening the cassettes is the risk that the technicians handling the cassettes will cut themselves. The significance of this risk is underscored by the fact that the electrophoresed biological materials are often body fluids which may be contaminated with infectious diseases, such as AIDS, hepatitis and herpes.

In one attempt to overcome this problem, U.S. Pat. No. 4,929,329 provides a cassette with a strip, having top and bottom tabs and being positioned on the face of the top glass plate for cooperation with a monofilament, loop-shaped spacer positioned between the two glass plates for facilitating the replacement of the monofilament spacers when reassembling and filling new cassettes. Unfortunately, the cassettes disclosed in U.S. Pat. No. 4,929,329 cannot be conveniently stacked atop one another when such a strip is positioned on the front faces of the top glass plates. In addition, the spacers selected are monofilaments in unconventional loop-shaped form, so that the strips can be connected to the spacers.

Consequently, there is a demand in the electrophoresis industry for electrophoresis gel slab cassettes which can be easily and conveniently assembled and opened following electrophoresis without having to resort to razor blades or knives, so that the gel slabs can be removed therefrom without infectious risk and processed for preparing and/or analyzing the biological molecules electrophoresed therein.

SUMMARY OF THE INVENTION

In brief, the present invention alleviates and overcomes certain of the above-mentioned problems and shortcomings of the present state of the electrophoresis cassette art through the discovery of novel electrophoresis gel slab cassettes, methods of opening the unique cassettes, and methods and a fixture for making the novel cassettes. The novel electrophoresis cassettes of the instant invention are uniquely designed so that they can be quickly and easily opened and the gel slabs removed therefrom following electrophoresis. Quite amazingly, the present invention permits the novel electrophoresis cassettes to be opened without the use of razor blades or sharp knives or having to peel tape therefrom as required with electrophoresis cassettes available hitherto. Even more amazingly, the present invention permits this to be accomplished without having to resort to placing strips on the outer faces of the front plates of the cassettes for cooperation with monofilament, loop-shaped spacers positioned between the plates, or having to use tape along the opposing vertical side edges of the plates to hold the plates together.

Generally speaking, a novel electrophoresis cassette of the instant invention includes two plates formed of a non-conducting material, such as glass, and at least one pull cord positioned between the vertical side edges of the plates for opening the cassette. In accordance with the present invention, the two plates are spaced apart from one another via spacers positioned in parallel relationship therebetween to form a space or gel slot into which a gel slab is ultimately formed and are held together with means, such as an adhesive, which extends along the left and right vertical side edges of the two plates and between the two plates. Uniquely, at least one pull cord is positioned along the left and/or right vertical side or on each vertical side of the plates between a spacer and the holding means on such respective sides for ripping through or rupturing the holding means following electrophoresis, so that the two plates can be easily opened and the gel slab cast therebetween can be removed for further analysis. Because the holding means can be advantageously broken by the pull cord(s), the electrophoresis cassettes of the instant invention can now be opened following electrophoresis without having to resort to the use of sharp objects or having to peel tape off of the vertical side edges. Thus, the risk of infection to the technicians associated with the use of the electrophoresis cassettes available heretofore has now been eliminated.

In accordance with the present invention, the holding means is preferably a soft-curing adhesive and more preferably a soft-curing adhesive having a fast cure rate which forms a seal between the vertical side edges of the plates, and the pull cord is in the form of a pull cord assembly when the front plate of an electrophoresis cassette is shorter in vertical height than the back plate. The pull cord assembly of the instant invention generally comprises a tab portion integrally connected to a tear strip portion. When assembled into a cassette, the tab portion is positioned above the shorter top plate and generally adjacent a vertical side edge thereof and the tear strip portion is positioned between the holding means and a spacer along the same vertical side edge. Nevertheless, it should be appreciated that other holding means, such as tape, and other pull cords may be selected so long as the objectives of the instant invention are not defeated. It should be further appreciated that the pull cords of the present invention should be formed of a material having a tensile strength sufficient to rip through or rupture the holding means.

In accordance with a further feature of the instant invention, the electrophoresis cassettes may include one or two pull cords. It should be appreciated that, when the cassettes are manufactured with two pull cords positioned along the opposite vertical side edges, the untorn pull cord and holding means along the opposite vertical side edges of the cassette cooperate with one another to uniquely act as a hinge about which the plates are opened. Nevertheless, it is believed that, when the holding means is a soft-curing adhesive and the cassette is manufactured with only one pull cord, the soft-curing adhesive along the unruptured vertical side edge will function adequately by itself as a hinge about which the plates are opened.

In accordance with a further feature of the instant invention, a novel fixture for assembling the electrophoresis cassettes of the present invention is disclosed. The fixture is uniquely designed to permit the electrophoresis cassettes of the present invention to be accurately, quickly and easily assembled so that the effectiveness of the pull cords and holding means are not diminished, especially when a soft-curing adhesive is selected to hold the plates together along their opposing vertical side edges.

Accordingly, it can now be appreciated by those versed in this art that the present invention provides a solution to the electrophoresis art that has long sought to overcome the shortcomings associated with electrophoresis cassettes available heretofore.

The above features and advantages of the present invention will be better understood with reference to the FIGS. and Detailed Description set out hereinbelow. It will also be understood that the electrophoresis cassettes, fixture and methods of this invention are exemplary only and are not to be regarded a limitations of this invention.

BRIEF DESCRIPTION OF THE FIGS.

Examples of the present invention will now be more fully described, with reference to the accompanying FIGS., wherein:

FIG. 1 is an exploded perspective view of an electrophoresis cassette of the instant invention;

FIG. 2 is a perspective view of the electrophoresis cassette illustrated in FIG. 1, but in an assembled relationship;

FIG. 3 is a partial cross-sectional view taken along lines 3—3 of the electrophoresis cassette illustrated in FIG. 2;

FIG. 9 is a fragmentary perspective view of an upper left corner of still another alternative electrophoresis cassette of the instant invention;

FIG. 10 is a perspective view of a fixture for assembling an electrophoresis cassette of the instant invention;

FIG. 11 is a top plan view of the fixture shown in FIG. 10 illustrating a stage of assembly of an electrophoresis cassette of the instant invention; and FIG. 12 is a top plan view of the fixture show in FIG. 10 illustrating yet another stage of assembly of an electrophoresis cassette of the instant invention.

DETAILED DESCRIPTION OF THE INVENTION

Figure 4:
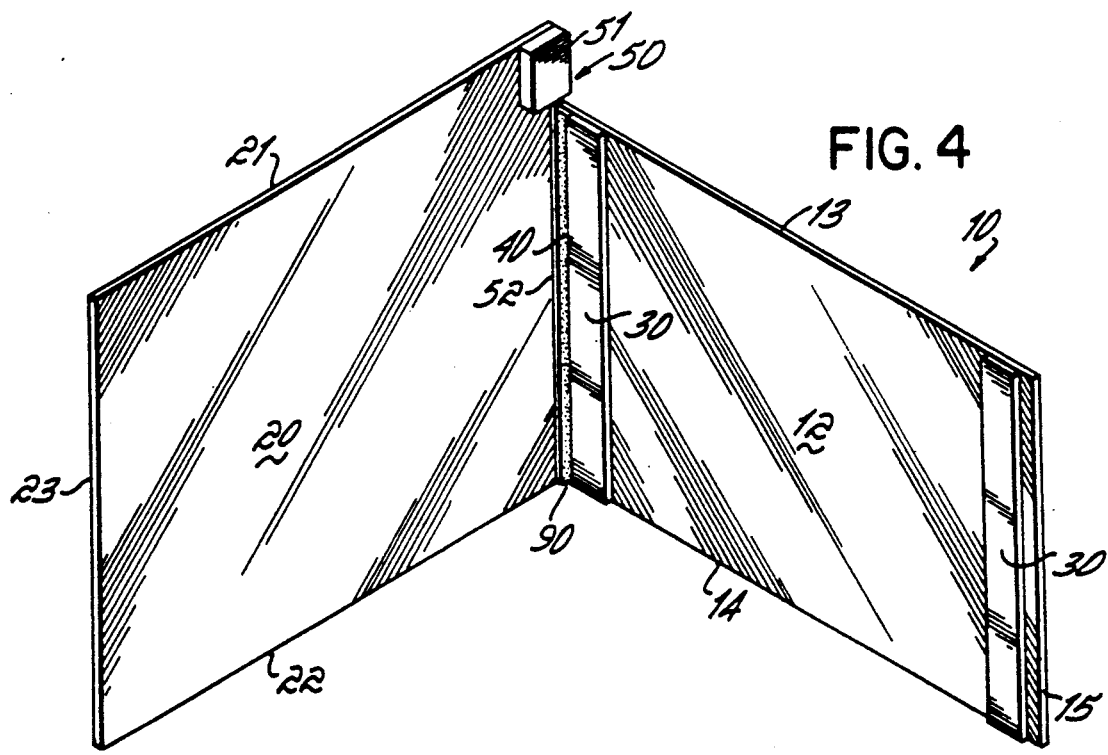
FIG. 4 is a perspective view of the electrophoresis cassette illustrated in a FIG. 2, but shown in a hinged-open position.

By way of illustrating and providing a more complete appreciation of the present invention and many of the attendant advantages thereof, the following detailed description is provided concerning the novel electrophoresis cassettes, the novel fixture for assembling the cassettes, and novel methods of utilization thereof.

Turning now to the FIGS. wherein like referenced numerals represent like structure and, in particular, to FIGS. 1–4, a preferred vertical electrophoresis cassette of the present invention, designated generally as 10, is shown. The vertical electrophoresis cassette 10 in this embodiment comprises a front flat glass plate 12 and a back flat glass plate 20, arranged vertically with upper edges 13 and 21, lower edges 14 and 22, left side edges 15 and 23, and right side edges 16 and 24, respectively. Front glass plate 12 is, for example, about 2.756 inches in vertical height, about 3.937 inches in horizontal width and about 0.040 inches in thickness. Back flat glass plate 20 has dimensions of, for example, about 3.150 inches in vertical height, about 3.937 inches in horizontal width and about 0.040 inches in thickness It should be understood, of course, that any suitable dimensions and shapes for the plates may be selected.

The left and right vertical spacers 30 are placed between the two flat glass plates 12 and 20 along, but inboard the two side vertical edges of each plate, 15, 23 and 16, 24, respectively, as shown in FIGS. 2–4. Spacers 30 are in a parallel relationship and are, for example, about 2.756 inches in vertical length, about 0.275 inches in horizontal width and about 0.040 inches in thickness. Vertical clamps (not shown) can be placed around the two side vertical edges of the glass plates 12 and 20, compressing the spacers 30 between the glass plates 12 and 20 to form a liquid-type seal during an electrophoresis run. Examples of such clamps are shown in U.S. Pat., Nos. 4,663,015, No. 4,732,657 and No. 4,773,984, which are incorporated herein by reference in their entireties.

A gel, across which electrophoretic separation takes place, can be positioned between the glass plates 12 and 20. Preferably, and as illustrated in FIGS. 1–4, the front glass plate 12 is vertically shorter than the back glass plate 20, and that the spacers 30, which can be made of any suitable material, such as Teflon glass, delrin, certain polyvinyl chlorides and the like, are the same vertical height as the front glass plate 12. As best illustrated in FIGS. 2 and 3, the vertical electrophoresis cassette 10, when the glass plates 12 and 20 are brought together in a planar fashion with spacers 30 therebetween, exhibits a horizontal gap the thickness of spacers 30. It is in this gap that the gel slab resides. Also, due to the unequal vertical height of glass plates 12 and 20, intimate contact of the uppermost end of a gel slab formed between the two glass plates 12 and 20 with a buffer solution in an upper tank or reservoir is effectively attained. It, of course, should be appreciated by those versed in this art that while it is preferable in accordance with the instant invention for the glass plates to have unequal vertical heights, it is not critical to the instant invention, as depicted by the alternative vertical electrophoresis cassettes in FIGS. 6 and 7. In addition, the present invention contemplates the use of any suitable electrophoresis medium, such as polyacrylamide and agarose gels, to form the gel slabs between the glass plates 12 and 20.

The vertical electrophoresis cassettes of the instant invention are preferably held together by strips of vertically extending adhesive 40 positioned inboard between the left and right vertical edges 15, 23 and 16, 24, respectively, of the glass plates 12 and 20, as shown in FIGS. 2-4. In accordance with the present invention, the adhesive preferably is a soft-curing adhesive with thixotropic properties, so that when the adhesive is initially applied between the glass plates 12 and 20, it will not run, i.e., it will not self-level. Moreover, the adhesives selected for use with the present invention should have a quick cure time or a cure time which can be effectively accelerated to reduce assemblage time. In addition, the adhesives selected for use with the present invention should preferably be clear and inexpensive. More importantly, because the electrophoresis cassettes are generally formed with glass plates and are exposed to various electrophoresis chemicals and gels, the adhesives should be capable of forming good bonds with glass and be resistant to such chemicals and gels when exposed thereto. In other words, the adhesives of the instant invention should have the ability to maintain their chemical integrity when exposed to the electrophoresis gels and chemicals and during an electrophoresis run.

Exemplary of a preferred adhesive in accordance with the instant invention is an acetoxy curing silicone adhesive, distributed under the trademark Nuva-Sil 83 by Loctite Corp., 705 North Mountain Road, Newington, Conn. 06111. It has been surprisingly discovered that the Nuva-Sil 83 adhesive is an inexpensive, soft-curing, clear, thixotropic adhesive which forms effective bonds with glass, and it is resistant to the electrophoresis chemicals and gels when exposed thereto. As a further advantage, the cure time of the Nuva-Sil 83 adhesive can be effectively accelerated by ultraviolet (UV) waves.

For example, when the Nuva-Sil 83 adhesive is cured using an F 450 Ultraviolet Lamp System available through Fusion Systems Corp., 7600 Standish Place, Rockville, Md. 20855, wherein the wavelength is about 380 nm, the lamp power output is about 300 watts/inch and the conveying speed is approximately 10 feet/minute, the cure time is about 2 seconds. It should be understood, however, that when such adhesive is cured at lamp power output of 250 mW/cm, the set up time is less than about 1 second and the complete cure time is under about 10 seconds.

Examples of other curing silicone adhesives which are believed to be suitable for use with the instant invention include other acetoxy curing silicone adhesives distributed under the trademarks Nuva-Sil 91 and Nuva-Sil 147, methoxy curing silicone adhesives distributed under the trademarks Nuva-Sil 84 and Nuva-Sil 88, and a curing silicone adhesive distributed under the trademark Nuva-Sil 76, all of which are available through the Loctite Corp. referenced hereinabove.

Other alternative adhesives that may be employed with the instant are room temperature vulcanizing (RTV) adhesives, such as Dow Corning adhesive, No. 732, Box 0994, Dept. A-6018, Midland, Mich. 48686, which, at about 50% relative humidity and at room temperature, the initial set up time is about 20 minutes with a full cure time of about 24 hours, and Loctite Corp. adhesive, No. 595 RTV silicone, 705 North Mountain Road Newington, Conn. 06111, which, at about 50% relative humidity and at room temperature, the initial set up time is about 1 hour with a full cure time of approximately 24 hours. While it is believed that these adhesives 40 are suitable for use, the RTV adhesives generally have slower cure times than the Nuva-Sil adhesive. Nevertheless, while any suitable adhesive may be employed with the instant invention, it should be appreciated by those of skill in the art that, when an adhesive is selected, its application properties, pre- and post-cure properties, and cure time properties must be taken into consideration so that the objectives of the instant invention are not defeated.

In addition, it should be appreciated by those versed in this art that the cure times of these as well as other adhesives suitable for use in the instant invention are dependent upon not only the curing systems or environments selected, but also the quantity of adhesive to be cured. Thus, while cure times may vary between adhesives and/or due to the amounts of adhesive used, the term "fast cure rate" as used herein means a cure time which is shorter than the cure time for an RTV adhesive when cured at about 50% relative humidity and at room temperature when cured between the two plates 12 and 20, and more particularly a cure time which is under about 10 seconds when cured between the two plates 12 and 20.

As further illustrated in FIGS. 1-4, a pull cord assembly 50 is positioned in the canals 78 formed between the vertical side edges 15, 23 and 16, 24 of glass plates 12 and 20 and inboard between glass plates 12 and 20 for ripping through the soft-cured adhesive 40 to open the glass plates 12 and 20 following an electrophoresis run. The pull cord assembly 50 comprises a pull tab 51 integrally connected to a tear strip 52. The vertical height of the tear strip 52 is preferably equal to the vertical height of the front glass plate 12, as shown in FIGS. 1-2 and 4. The width and thickness of tear strip 52 is preferably less than the thickness of spacers 30 and the canals 78 formed inboard by spacers 30 and the glass plates 12 and 20, as best depicted in FIG. 3, so that the soft-curing adhesive 40 can effectively hold pull tab assembly 50 in place. The vertical height of pull tab 51 is preferably equal to the difference in height between back glass plate 20 and front glass plate 12, whereas the thickness of pull tab 51 is preferably equal to the thickness of spacers 30 and front glass plate 12, so that a flush surface will be formed between front glass plate 12 and pull tab 51 when pull cord assembly 50 is in an assembled configuration, as shown in FIG. 2. As to the width of pull tab 51, it preferably should be equal to the width of tear strip 52 and spacers 30. Typical dimensions for pull cord assembly 50 are as follows: pull tab 51 is about 0.394 inches in vertical length, about 0.315 inches in horizontal width, and about 0.080 inches in thickness; and tear strip 52 is about 2.756 inches in vertical length, about 0.023 inches in horizontal width, and about 0.023 inches in thickness.

The material selected to form pull cord assembly 50 should have a strength sufficient to tear through adhesive 40 without breaking so that the two glass plates 12 and 20 can be opened without having to resort to cutting the adhesive with a sharp instrument, such as a razor blade or knife. Likewise, the adhesive 40 should be soft-curing, as indicated hereinbefore, and have a tensile strength and sheer strength which permits the pull cord assembly 50 to rip therethrough.

In accordance with a further feature of the instant invention, when such a soft-curing adhesive is employed and the cassette is opened along the vertical side edges on one side of the plates 12 and 20 with a pull cord assembly 50 of the instant invention, the adhesive and pull cord assembly 50 remaining intact along the opposite vertical side edges of the plates 12 and 20 will uniquely function as a hinge 90 about which the front and back glass plates 12 and 20, respectively, may be opened, as shown in FIG. 4.

There are a number of materials such as nylon, urethane, or certain other polymers which may be used successfully, in the manufacture of this type of pull cord assembly 50. Mechanical properties of materials used should be such that the tear strip 52 may function as a tear strip without breaking, i.e., has sufficient tensile and sheer strength while maintaining an adequate amount of flexibility. Compatibility with the electrophoresis gels and high die-electric strength are the other material considerations. High die-electric strength is important for the gel must be the only conductor between upper and lower buffer solutions when the electrophoresis cassettes are placed in a device for running.

Exemplary of a preferred material to form pull cord assembly 50 is a Polythane STE #73D high performance cast urethane distributed by Polaroid, 549 Technology Square, Cambridge, Mass. 02139. The physical properties of the Polythane STE #73D are as follows:

| | |
|---|---|
| hardness, shore D | 73 |
| tensile strength, psi | 8800 |
| elongation % | 230 |
| tear strength, die C | 800 |
| rebound % | 43 |
| 100% modulus, psi | 4800 |

The pull tab 51 and the tear strip 52 are preferably molded as one piece to form the pull cord assembly 50, and a right and left orientation are done simultaneously. Initial production of the pull cord assemblies 50 may be accomplished using a two part compression mold, the lower portion of the mold housing the entire mold cavity, and molding several pairs of pull cord assemblies at one time. However, because this method is costly as well as slow, a preferred method of manufacture, while it may not be the only viable one is to injection mold the assemblies in accordance with techniques well-known to those in the injection molding art. Using an injection molding technique, as many multiples can be done at once as the constraints of the molding machine will permit.

Figure 5:
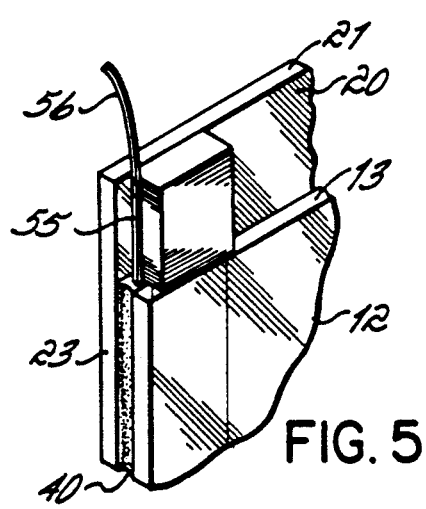
FIG. 5 is a fragmentary perspective view of an upper left corner of an alternative electrophoresis cassette of the instant invention.
Figure 6:
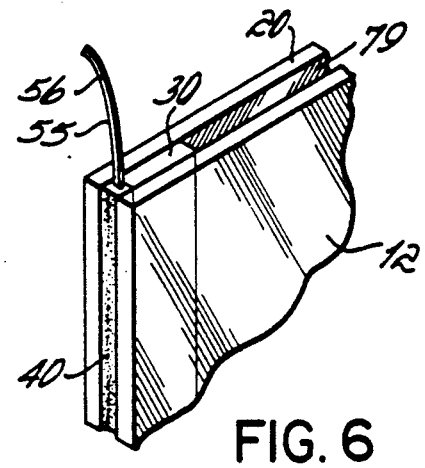
FIG. 6 is a fragmentary perspective view of an upper left corner of another alternative electrophoresis cassette of the instant invention.
Figure 7:
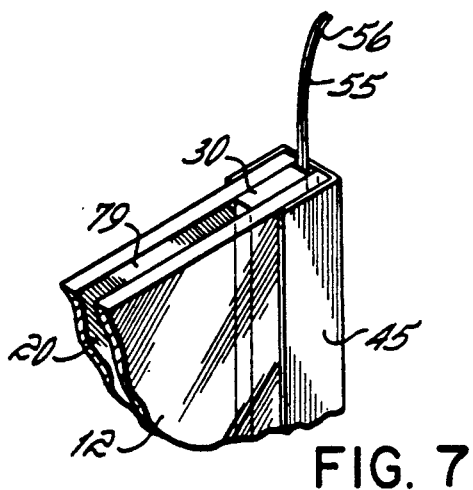
FIG. 7 is a fragmentary perspective view of an upper right corner of yet another alternative electrophoresis cassette of the instant invention.

In accordance with a further feature of the instant invention, the present invention contemplates substituting rip cords 55 for pull cord assemblies 50, as illustrated in FIGS. 5-7 and 9. Rip cord 55 should preferably have a vertical length which exceeds the vertical height of front plate 12 when front plate 12 is shorter than back plate 20, as shown in FIGS. 5 and 9, and a vertical length which exceeds the vertical height of back plate 20 when back plate 20 is of the same vertical height as front plate 12, as depicted in FIGS. 6 and 7, so that a portion 56 of rip cord 55 extends outward from the glass plates for gripping by a technician to open the glass plate. In such an arrangement, however, it should be appreciated that, if front glass plate 12 is shorter in vertical height than back glass plate 20, as shown in FIGS. 5 and 8, a separate tab 56 of suitable dimension should be affixed to the back glass plate 20 and adjacent the upper edge 13 of front glass plate 12 to provide a flush surface for the clamps to insure that a water-tight seal is maintained during an electrophoresis run.

Figure 8:
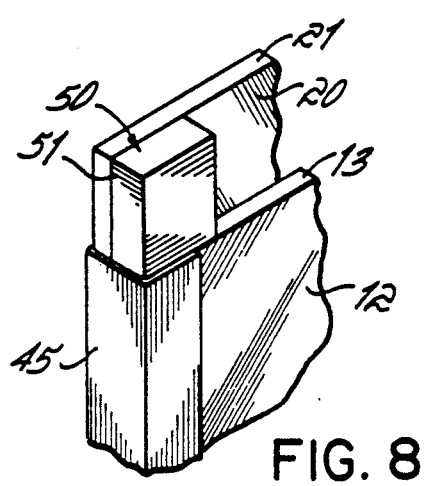
FIG. 8 is a fragmentary perspective view of an upper left corner of still another alternative electrophoresis cassette of the instant invention.

As an alternative to the use of a soft-curing adhesive to hold the front and back glass plates 12 and 20, respectively, together, strips of vertically extending adhesive tape 45 which overlay the vertical side edges of the glass plates 12 and 20 may be used, as shown in FIGS. 7-9. According to this feature of the present invention, adhesive tape 45 may be used with either a pull cord assembly 50, as shown in FIG. 8, or a rip cord 55, as shown in FIGS. 7 and 9. Like the soft-curing adhesive 40, the adhesive tape 45 should have a tensile strength and sheer strength sufficient to permit a pull cord assembly 50 or a rip cord 55 to tear easily therethrough without having to resort to a sharp instrument, such as a razor blade or knife, so that the glass plates may be opened following an electrophoresis run. Moreover, the adhesive tape 45 should be resistant to the electrophoresis chemicals and gels and should be non-conductive. An example of an adhesive tape which is believed to be suitable for use is No. 6800, yellow polyester film tape by Decker, 6 Stuart, Fairfield, N.J. 07006.

While the novel vertical electrophoresis cassettes 10 of the instant invention may be assembled by various procedures, one preferred method involves the use of a novel fixture, designated generally as 80, as depicted in FIGS. 10-12. Fixture 80 comprises left and right vertical shoulders 81 and 82, respectively, mounted atop a support 83 via Allen type screws 84. Mounted between left and right vertical shoulders 81 and 82 is horizontal base 85. Horizontal base 85, like left and right vertical shoulders 81 and 82, respectively, is mounted to support 83 via Allen type screws 84. Left and right vertical shoulders 81 and 82, respectively, of fixture 80 are provided with vertical grooves 86 and 87 for forming recesses 88 and 89, respectively, with support 83. It should be understood by those versed in this art that the dimensions of recesses 88 and 89 should be of sizes sufficient to receive therein one vertical side edge of back glass plate 20 to align spacers 30, so that adhesive 40 and tear strip 52 of pull cord assembly 50 or rip cord 55 can be effectively positioned inboard in the canal 78 formed between the two glass plates 12 and 20 along their vertical side edges, as shown in FIG. 3. More particularly, the vertical height of recesses 88 and 89 should be at least slightly greater than the thickness of back glass plate 20. The horizontal width or depth of recesses 88 and 89 should be slightly wider than the horizontal width of tear strip 52 or rip cord 55. Exemplary dimensions of recesses 88 and 89 when cassettes 10 are formed with pull cord assembly 50 or rip cord 55 are as follows: vertical height is about 0.050 inches and the horizontal width or depth is about 0.040 inches.

To assemble the cassettes 10 according to the instant invention, the left vertical side edge 23 of back glass plate 20 is positioned in recess 88 in fixture 80, as shown in FIG. 11. A pressure sensitive adhesive, such as 75 Repositionable Adhesive distributed by Adhesives, Coatings and Sealers Division of 3M, St. Paul, Minn. 55144, is first applied to both sides of spacers 30. The left spacer 30 is then attached to back glass plate 20, using fixture 80 to position the left spacer 30 the desired distance from the left vertical edge 23 and flush with the bottom edge 22 of the back glass plate 20.

Once left spacer 30 has been positioned on back glass plate 20 and flush with the left shoulder 81 and base 85, back glass plate 20 is then inserted into recess 89 formed between right shoulder 82 and support 83 with bottom edge 22 of back glass plate 20 abutting base 85. The right spacer 30 can then be attached to back glass plate 20, using fixture 80 to position the right spacer 30 the desired distance from the vertical right side edge 24 and flush with bottom edge 22 of the back glass plate 20. In other words, right spacer 30 is positioned on back glass plate 20 and flush against right shoulder 82 and base 85.

Front glass plate 12 may then be attached to the left and right spacers 30 positioned on back glass plate 20 using the fixture 80, so that the vertical left and right edges 15 and 16 and bottom edge 14 of front glass plate 12 is in alignment with the left and right vertical edges 23 and 24 and bottom edge 22 of the back glass plate 20, as shown in FIG. 12.

Following positioning of the front glass plate 12 onto spacers 30, the pressure sensitive adhesive should be applied to the back side of the molded pull tab 51 of pull cord assembly 50. The molded pull tab 51 is then attached to the back glass plate 20, so that the tear strip 52 of each pull tab assembly 50 sits in the canal 78 flush to the outside edge of each spacer 30, and each pull tab 51 sits flush to the top edge of the respective spacers 30 and the upper edge 13 of front glass plate 12.

Using an automatic fluid dispenser, such as an EFD-1000 Series Automatic Fluid Dispenser, the soft-curing adhesive 40 is applied into each side canal 78 that has been formed by the front glass plate 12, back glass plate 20 and spacers 30. These canals 78 also house the tear strips 52 or rip cords 55 which are sitting flush to the outside edge of the spacers 30. The adhesive 40 should be applied from the upper edge 13 to the bottom edge 14 of front glass plate 12.

Using a flat spatula or similar tool, the excess adhesive 40 should be removed by running the spatula down the opposing vertical side edges 15, 23 and 16, 24 of the cassettes 10 where the adhesive 40 has been applied. In addition to removing the excess adhesive, this allows the adhesive 40 to better fill the canal 78 before curing. To cure a soft-curing adhesive, such as the Nuva-Sil 83 adhesive, the adhesived canals 78 of cassette 10 are exposed to a suitable UV source that will provide adequate curing intensity at the proper wavelength, as recommended by the manufacturer. In the event that an RTV adhesive is selected, such soft-curing adhesive may be cured by exposing it to air at room temperature and at about 50% relative humidity.

Once the cassettes 10 of the instant invention have been formed, a selected electrophoresis gel may be introduced into the gap 79 formed between front glass plate 12 and back glass plate 20 via spacers 30. Before pouring a selected gradient gel into cassette 10, a specified well-forming comb (not shown) is usually positioned inside the top of the cell area or gap 79. This comb drops approximately one centimeter into the cell area or gap 79 and facilitates the forming of lane wells in the gel during polymerization. Standard pouring of single concentration and gradient gels can be performed in cassettes 10 using, for example, a Hoefar Scientific SE 275 Mighty Small Four-Gel Caster or 3E 215 Mighty Small Multiple Gel Caster.

The SE 215 and SE 275 casters can form both single concentration and gradient gels. To form single concentration gels, the monomer gel solution is poured into the top of the assembled casting chamber or gap 79 of cassette 10. The gel solution will flow into all the sandwiches equally. To form gradient gels, the gradient from a gradient maker is pumped into the inlet at the bottom of the casting chamber or gap 79 of cassette 10. The gradient will stabilize in the V-shaped cavity before entering the sandwiches of cassette 10. It should of course be understood by those versed in this art that other techniques to fill the cell area or gap 79 formed by the front glass plate 12, back glass plate 20 and spacers may be used.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced therein.

Having described our invention, we claim:

1. An electrophoresis cassette, comprising:
   a front electrically nonconductive flat plate having two faces which are substantially parallel to one another and having top and bottom edges and left and right vertical side edges;
   a back electrically nonconductive flat plate having two faces which are substantially parallel to one another and having top and bottom edges and left and right vertical side edges;
   a pair of electrically nonconductive spacers for spacing said plates apart and being generally parallel with one another to form a gel slot between said plates;
   electrically nonconductive adhesive means for holding said front and back plates in a fixed relationship with each other wherein the faces of the front plate are substantially parallel to the faces of the back plate and the confronting faces of the plates are separated by a distance determined substantially by said spacers to form said gel slot, said adhesive means being positioned along the left and right vertical side edges of said front and back plates and providing a seal between said front and back plates along the left and right vertical side edges thereof; and
   a pull cord assembly for enabling said cassette to be opened, said pull cord assembly comprising a grippable element integrally connected to an electrically nonconductive tear strip, said tear strip being nonintegral with said plates and positioned inwardly of one of its associated adhesive means and between planes containing said front and back plates, said tear strip ripping through said associated adhesive means when said grippable element is pulled to facilitate opening of said cassette.

2. An electrophoresis cassette as recited in claim 1, said cassette further including a gel slab sandwiched between said front and back plates in the gel slot.

3. An electrophoresis cassette as recited in claim 1, said holding means being a soft-curing adhesive.

4. An electrophoresis cassette as recited in claim 3, said soft-curing adhesive being an acetoxy curing silicone adhesive.

5. An electrophoresis cassette as recited in claim 1, said holding means being an adhesive tape.

6. A method of opening an electrophoresis cassette formed with a pair of opposed plates whose respective confronting faces are separated from one another by spacers and held together and sealed by adhesive means positioned along the vertical side edges of the plates, said method comprising:

grabbing a pull tab integral with a tear strip of a pull cord assembly in which the tear strip is positioned between one of the spacers and the associated adhesive means and planes containing the plates; and pulling the pull tab so that the tear strip tears through the adhesive means along its associated vertical side edge on one side of the plates so that the cassette can be opened.

7. An electrophoresis cassette, comprising:

a front flat electrically nonconductive plate having two faces which are substantially parallel to one another and having top and bottom edges and left and right vertical side edges;

a back flat electrically nonconductive plate having two faces which are substantially parallel to one another and having top and bottom edges and left and right vertical side edges;

a pair of electrically nonconductive spacers for spacing said plates apart and being generally parallel with one another to form a gel slot between said plates;

an electrically nonconductive adhesive for holding said front and back plates in a fixed relationship with each other wherein the front and back plates are substantially parallel and the confronting faces of the plates are separated by a distance determined substantially by said spacers to form the gel slot, said adhesive being soft-curing adhesive having a fast cure rate and the ability to retain its chemical integrity while being exposed to electrophoresis chemicals during an electrophoresis run, said adhesive further being positioned along the left and right vertical side edges of said front and back plates and providing a seal between said front and back plates; and electrically nonconductive tear means nonintegral with the plates which is positioned for ripping outwardly through said adhesive along at least one of said vertical side edges so that said cassette may be opened when said tear means is pulled.

8. An electrophoresis cassette as recited in claim 7, said adhesive being an acetoxy curing silicone adhesive.

9. An electrophoresis cassette as recited in claim 7, said cassette further including a gel slab sandwiched between said front and back plates in the gel slot.

10. An electrophoresis cassette as recited in claim 7, said tear means being a pull cord assembly, said pull cord assembly comprising a pull tab integrally connected to an electrically nonconductive tear strip, said tear strip being positioned between planes containing said front and back plates along at least one of their vertical side edges and between said adhesive and at least one of said spacers.

11. An electrophoresis cassette as recited in claim 7, said tear means being an electrically nonconductive rip cord, said rip cord being positioned between planes containing said front and back plates along at least one of their said vertical side edges and between said adhesive and said spacer.

12. An electrophoresis cassette as recited in claim 7, said adhesive having cure time of less than about 10 seconds.

13. An electrophoresis cassette as recited in claim 7, said adhesive being a methoxy curing silicone adhesive.

14. An electrophoresis cassette as recited in claim 7, said adhesive being a curing silicone adhesive.

15. The apparatus of claims 1 or 3 or 5 wherein the height of the front plate is less than that of the back plate to vertically space the top edges of the front and back plates a specified distance apart, and wherein the pull tab is located above one of the spacers with its inner surface contacting the inner face of the back plate and wherein the pull tab has a thickness measured perpendicular to the plate faces which is substantially equal to the collective thicknesses of the spacer and the front plate whereby the outer face of the front plate is substantially flush with the outer surface of the pull tab.

16. The apparatus of claim 15 wherein the height of the pull tab measured vertically is substantially equal to said specified distance between the top edges of said front and back plates whereby the upper edges of said pull tab and back plate are substantially flush.

* * * * *

UNITED STATES PATENT AND TRADEMARK OFFICE
CERTIFICATE OF CORRECTION

PATENT NO.   :   5,186,807
DATED        :   February 16, 1993
INVENTOR(S) :   David P. Sanford, Bruce R. Turner, Richard J. Heim It is certified that error appears in the above-identified patent and that said Letters Patent is hereby corrected as shown below:

Col. 3, line 15, "based o" should be  -- based on --.

Col. 6, line 10, "show" should be  -- shown --.

Col. 8, line 11, insert a comma after "Road".

Col. 11, line 68, "Hoefar" should be  -- Hoefer --.

Col. 12, line 1, "3E 215" should be  --SE 215 --.

Col. 14. line 29, "claims 1 or 3 or 5" should be
    -- claims 1 or 3 or 5 or 7 --.

Signed and Sealed this

Twenty-second Day of March, 1994

Attest:

BRUCE LEHMAN

*Attesting Officer*     *Commissioner of Patents and Trademarks*